US006284913B1

(12) United States Patent
Fransson et al.

(10) Patent No.: US 6,284,913 B1
(45) Date of Patent: Sep. 4, 2001

(54) SELECTIVE HYDROGENATION OF A $C_3$-$C_5$ ALKYL ALCHOL

(75) Inventors: Patric Fransson, Huddinge; Magnus Sjögren, Stockholm, both of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/341,981

(22) PCT Filed: Jun. 10, 1999

(86) PCT No.: PCT/SE99/01032

§ 371 Date: Jul. 22, 1999

§ 102(e) Date: Jul. 22, 1999

(87) PCT Pub. No.: WO99/64391

PCT Pub. Date: Dec. 16, 1999

(30) Foreign Application Priority Data

Jun. 11, 1998 (SE) .................................................. 9802074

(51) Int. Cl.⁷ ................................................. C07C 255/00
(52) U.S. Cl. ............................................................ 558/422
(58) Field of Search ............................................... 558/422

(56) References Cited

U.S. PATENT DOCUMENTS 3,050,544   8/1962   Pietrusza et al. .

FOREIGN PATENT DOCUMENTS 814631      6/1959   (GB) .
1 226 187   3/1971   (GB) .
49085041    8/1974   (JP) .

OTHER PUBLICATIONS

STN International, CAPLUS Database, Chemical Abstracts Service, (Columbus, Ohio), No. 1998:498623; abstract of JP 10–204048 (Aug. 4, 1998).*
STN International, CAPLUS Database, Chemical Abstracts Service, (Columbus, Ohio), No. 1998:543045; abstract of WO 98/33766 (Aug. 6, 1998).*
Rylander, P., "Catalytic Hydrogenation over Platinum Metals," Academic Press, New York (1967) at p. 218.
McKay et al, J. Am. Chem. Soc., vol. 81, p. 4328 (1959).
Short et al, J. Med. Chem., vol. 10, p. 833 (1967).
Goldberg et al, J. Chem. Soc., p. 1369 (1947)

* cited by examiner

Primary Examiner—Deborah C. Lambkin
(74) Attorney, Agent, or Firm—Nixon & Vanderhye

(57) ABSTRACT

There is provided lower alkanesulphonate salts of cyanobenzylamines, which salts may be produced via a selective recrystallisation process. The salts may be produced advantageously following the selective hydrogenation of a dicyanobenzene to a cyanobenzylamine in the presence of a $C_{3-5}$ alkyl alcohol.

15 Claims, No Drawings

SELECTIVE HYDROGENATION OF A $C_3$-$C_5$ ALKYL ALCHOL

This appln is a 371 of PCT/SE99/01032 Jun. 10, 1999.

1. Field of the Invention

This invention relates to novel salts of cyanobenzylamines (CBAs), and to processes which may be used to produce such salts.

2. Prior Art

The selective hydrogenation of 1,4-dicyanobenzene to form 4-cyanobenzylamine (4-CBA) is a well known reaction.

For example, UK Patent No. 814,631 and Japanese Patent Application No. 49085041 both describe the hydrogenation of 1,4-dicyanobenzene in the presence of a palladium or a platinum catalyst, ammonia and, in the latter case, an inorganic alkali.

The hydrogenation of 1,4-dicyanobenzene in the presence of a palladium catalyst using methanol as a solvent has also been described in U.S. Pat. No. 3,050,544 and *Catalytic Hydrogenation over Platinum Metals,* Rylander, P., Academic Press, N.Y. (1967) at page 218.

None of these prior art documents refer to the use of a $C_{3-5}$ alkyl alcohol as a solvent.

Furthermore, in all of the abovementioned prior art documents, 4-CBA is isolated in the form of a free base. None disclose or suggest the isolation of 4-CBA in the form of a salt following its formation.

Salts of CBAs are known in the art, including the hydrochloride salt of 4-CBA (see, for example, McKay et al, J. Am. Chem. Soc. (1959) 81, 4328, Short et al, J. Med. Chem. (1967) 10, 833 and Goldberg et al, J. Chem. Soc. (1947) 1369). However, no CBA has ever been isolated in the form an alkanesulphonate salt.

DESCRIPTION OF THE INVENTION

We have found, surprisingly, that CBAs may be readily isolated in a chemically pure form, and in high yields, in the form of lower alkanesulphonate salts.

According to a first aspect of the invention there is provided a lower alkanesulphonate salt of a CBA. Lower alkanesulphonate salts of CBAs are referred to hereinafter as "the salts of the invention".

Lower alkanesulphonate salts which have been found to be useful include linear, branched or cyclic $C_{1-6}$ alkanesulphonate salts, preferably $C_{1-3}$ alkanesulphonate, and especially ethane- and methanesulphonate, salts. Toluenesulphonate salts may also be mentioned.

CBAs which may be mentioned include those which are unsubstituted or those in which one or both of the two available hydrogen atoms on the methylene group between the benzene ring and the amino group in the CBA, and/or one or more of the four available hydrogen atoms on the benzene ring, are replaced by a substituent. Substituents which may be mentioned include halo (e.g. fluoro, chloro, bromo or iodo); lower (e.g. linear or branched $C_{1-4}$) alkyl (which alkyl group is optionally substituted by one or more halo group); hydroxy; lower (e.g. linear or branched $C_{1-4}$) alkoxy; —O(CH$_2$)$_p$C(O)N(R$^a$)(R$^b$) (in which p is 0, 1, 2, 3 or 4, and R$^a$ and R$^b$ independently represent H, lower (e.g. linear or branched $C_{1-6}$) alkyl or lower (e.g. $C_{3-7}$) cycloalkyl); N(R$^c$)R$^d$ (in which R and R$^d$ independently represent H, lower (e.g. linear or branched $C_{1-4}$) alkyl or C(O)R$^e$ (in which R$^e$ represents H or lower (e.g. linear or branched $C_{1-4}$) alkyl)); or SR$^f$ (in which R$^f$ represents H or lower (e.g. linear or branched $C_{1-4}$) alkyl). Such substituted CBAs are known in the art or may be prepared using known techniques.

Preferred salts of the invention include the lower alkanesulphonate salts of 4-CBAs, particularly unsubstituted 4-CBA.

The salts of the invention may be prepared readily and advantageously via the selective crystallisation of a CBA with a lower alkanesulphonic acid.

According to a further aspect of the invention there is provided a process for the production of a salt of the invention which comprises selectively crystallising a CBA with a lower alkanesulphonic acid.

Suitable solvents which may be used in the selective crystallisation include lower alkyl alcohols such as $C_{1-6}$ alkyl alcohols (e.g. methanol, ethanol, n-propanol, iso-propanol, butanol) and mixtures thereof.

Crystallisation of salts of the invention may be achieved by attaining supersaturation in a solution of a CBA and a lower alkanesulphonic acid (e.g. by cooling to supersaturation temperature and/or by solvent evaporation). Final crystallisation temperatures depend upon the concentration of the salt in solution, and upon the solvent system which is used but, for the abovementioned solvent systems, temperatures are typically in the range −20 to 30° C., for example 0° C. to 25° C.

Crystallisation may also be effected with or without seeding with crystals of the appropriate salt of the invention.

The crystalline salt may be isolated using techniques which are well known to those skilled in the art, for example decanting, filtering or centrifuging.

We have found that, by employing the selective crystallisation as described herein, it is possible to produce salts of the invention with a chemical purity of above 90%, for example above 95% and, in particular, above 96%, depending upon the purity of the CBA to be crystallised in the first instance.

Further purification of the salt may be effected using techniques which are well known to those skilled in the art. For example impurities may be removed by way of adding base to an aqueous solution of the salt and then partitioning between aqueous and organic phases. Impurities may also be removed by way of recrystallisation from an appropriate solvent system (e.g. a lower (e.g. $C_{1-6}$) alkyl alcohol, such as methanol, propanol (e.g. iso-propanol), butanol or, particularly, ethanol, or a combination of these solvents), and/or as described hereinafter. Suitable temperatures for the recrystallisation depend upon the concentration of the salt in solution, and upon the solvent system which is used but, for the abovementioned solvent systems, temperatures are typically in the range −20 to 35° C., for example −5° C. to 30° C., preferably 5 to 30° C.

The purification of salts of the invention may also comprise filtering a hot (i.e. above room temperature) solution of salt in order to remove insoluble impurities. (This "hot" filtration may also be carried out on an impure solution of CBA, before the selective crystallisation is carried out.)

Although salts of the invention may be isolated and stored if desired, liberation of the CBA from the salt following selective crystallisation may be achieved by displacing the lower alkanesulphonic acid from the salt using techniques which are well known to those skilled in the art. CBA may also be liberated by two-phase extraction, for example by adding base (e.g. metal hydroxide, metal alkoxide, metal carbonate or metal hydrogen carbonate) to a biphasic (organic/aqueous) mixture including the salt, separation and standard work up. The CBA may be further purified using conventional techniques (e.g. recrystallisation from an appropriate solvent, distillation, or chromatography, or by purifying by making an appropriate salt (e.g. an alkanesulphonate or a hydrate), in accordance with techniques which are well known to those skilled in the art).

However, in view of their chemical stability, salts of the invention may be used in subsequent reactions to form other chemical compounds without the need for prior liberation of the free amine.

Though the selective crystallisation process described hereinbefore may be used to provide salts of the invention in a variety of stoichiometric ratios, preferred ratios of alkanesulphonate to cyanobenzylamine are in the range 1.0:0.9 to 1.0:1.1, preferably 1.0:0.95 to 1.0:1.05.

Salts of the invention have been found to possess surprising advantages over free CBAs, and over other salts of CBAs, such as hydrochloride salts. Advantages which may be mentioned include chemical stability. Further, we have found that salts of the invention may be crystallised in good yields, and in higher purity than other salts (such as hydrochloride salts), from a concentrated solution of the salt.

Additional advantages, as compared to corresponding hydrochloride salts, include higher solubility in organic solvents, such as lower alkyl alcohols, acetates and ketones, as well as the avoidance of well known disadvantages which are associated with the use of gaseous HCl in the formation of such salts.

Further, salts of the invention may have the advantage that they (and, consequently, CBAs) may be prepared in higher yields, with greater purity, in less time, more conveniently, and at a lower cost, than CBA salts (and CBAs) prepared previously.

We have also found, advantageously, that salts of the invention may be prepared in a convenient fashion following the selective hydrogenation of corresponding dicyanobenzenes (e.g. 1,4-dicyanobenzenes), especially when the hydrogenation reaction is carried out in the presence of a linear or branched $C_{3-5}$ alkyl alcohol as solvent.

According to a further aspect of the invention there is provided a process for the preparation of a CBA, comprising a selective hydrogenation of a dicyanobenzene, which hydrogenation is carried out in the presence of a $C_{3-5}$ alkyl alcohol, such a propanol or butanol, particularly iso-propanol.

Hydrogenation of dicyanobenzenes in the presence of a $C_{3-5}$ alkyl alcohol as solvent may be carried out under standard conditions, for example at between 0° and 70° C., especially 20° and 60° C., and particularly 25° and 55° C., at between around 3 and 7 atmospheres hydrogen pressure, and in the presence of standard hydrogenation catalysts such as palladium, or platinunr, on activated carbon.

The hydrogenation as described herein has been found to have the advantage that unreacted starting material(s) (which may be only partially dissolved in the reaction mixture) can be recycled in order to increase the overall yield of the hydrogenation. Further, the CBA so formed may subsequently be converted readily to a lower alkanesulphonate salt by way of a selective crystallisation as described herein. Thus, lower alkanesulphonate salts of CBAs also have the advantage that they may be readily formed in situ by way of a selective hydrogenation as described herein, followed by a selective crystallisation as described herein (i.e. without the need to isolate CBA prior to crystallisation).

Following the hydrogenation, the reaction mixture may be filtered (at or above room temperature) and/or a portion of the reaction solvent removed by evaporation, in order to remove unreacted starting material, chemical reagents and by-products, and in order to increase the yield. By-products of the hydrogenation reaction may also be removed by the preliminary addition of lower alkanesulphonic acid (the amount of acid that needs to be added to remove by-products may be predetermined, for example as described hereinafter), followed by filtration or centrifugation. The selective crystallisation of the CBA remaining in solution may then be carried out as described herein via the addition of lower alkanesulphonic acid.

The salts of the invention are useful as chemical intermediates. In particular they may be used in peptide coupling reactions to form low molecular weight peptide based compounds, which may themselves have a variety of uses, e.g. as pharmaceutically-useful substances. Further, the cyano group of the CBA may be converted into an amidino (—C(NH)NH$_2$), or a hydroxyamidino (—C(NOH)NH$_2$), group using techniques that are well known to those skilled in the art. This may be done before or after carrying out a peptide coupling reaction in order to obtain peptide-based compounds including a para-amidino benzylamine (—Pab—H) or a para-hydroxyamidino benzylamine (—Pab—OH) moiety.

The invention is illustrated, but in no way limited, by the following examples.

The hydrogenation reaction was monitored by monitoring the amount of H$_2$ gas consumed during the reaction and/or by standard chromatographic techniques. The purity of CBA in the reaction mixture was monitored by GC or LC. The purity of salts of the invention was monitored by standard column chromatographic techniques (such as HPLC).

EXAMPLE 1

Preparation of Crude 4-Cyanobenzylammonium Methanesulphonate (Small Scale)

1,4-Dicyanobenzene (2.0 g; 15.6 mmol) and palladium on activated carbon (1.0 mol % Pd/1,4-dicyanobenzene) were suspended in iso-propanol (30 mL) at 50° C. Hydrogen was continuously added at a pressure of 6 atm. When the desired conversion was obtained (2.5 h), the hydrogen was replaced by nitrogen and the solid material (Pd/C and unreacted 1,4-dicyanobenzene) was filtered off. Methanesulphonic acid (1.5 g; 15.6 mmol) was added to the clear solution. The crystals which formed were centrifuged, washed with a small amount iso-propanol and dried to yield 2.77 g (79%) of 4-cyanobenzylammonium methanesulphonate with a HPLC purity of 91.2 ae %.

$^1$H NMR (DMSO-d$_6$): δ 2.35 (3H, s), 4.16 (2H, s), 7.67 (2H, d), 7.93 (2H, d), 8.29 (3H, s)

$^{13}$C NMR (DMSO-d$_6$): δ 39.20, 42.70, 111.45, 117.70, 127.37, 132.30, 142.20

EXAMPLE 2

Preparation of Crude 4-Cyanobenzylammonium Methanesulphonate (Large Scale)

1,4-Dicyanobenzene (15.0 kg; 115 mol), palladium on activated carbon (0.8 mol % Pd/1,4-dicyanobenzene) was suspended in iso-propanol (285 L) at 30° C. Hydrogen was continuously added at a pressure of 6 atm. When the desired conversion was obtained (2.3 h) the hydrogen was replaced by nitrogen, the temperature was lowered to 20° C. and the solid material (Pd/C and unreacted 1,4-dicyanobenzene) was filtered off. The volume of the clear reaction mixture was reduced by ⅓ under vacuum.

An analysis of the remaining solution was performed to establish the amount of 1,4-di(aminomethyl)benzene impurity. Two mole equivalents of methanesulphonic acid at 20°

C. were added in respect of the determined amount of 1,4-di(aminomethyl)benzene. The slurry including 1,4-di(ammoniummethyl)benzene bismethanesulphonate which formed was filtered off.

One equivalent of methanesulphonic acid was added to the resultant clear solution. The crystals which formed were centrifuged, washed with a small amount iso-propanol (29 L) and dried under vacuum at about 50° C. to yield 16.0 kg (61%) of 4-cyanobenzylammonium methanesulphonate with a HPLC purity of 96.2 ae %.

EXAMPLE 3
Purification of Crude 4-Cyanobenzylammonium Methanesulphonate 1,4-Cyanobenzylammonium methanesulphonate, prepared according to the method described in Example 1, was found to contain large amounts of dimeric analogues. It was purified in the following manner:

Approximately 170 g of 4-cyanobenzylammonium methanesulphonate with approximately 8% of dimeric analogues was dissolved in water (680 mL) and toluene (450 mL). Aqueous sodium hydroxide was added to the two phase system until the dimeric analogues had been extracted into the organic phase. The two phases were separated and ethyl acetate (680 mL) was added followed by aqueous sodium hydroxide until a pH value of 11 was attained. The phases were separated and the organic phase was evaporated in vacuo. The organic material was dissolved in iso-propanol (500 mL) at ambient temperature. Methanesulphonic acid (48.4 mL) was then added. A slurry was formed immediately and the crystals were filtered and dried at 65° C. to yield 107 g of 4-cyanobenzylammonium methanesulphonate which was recrystallised as in Example 5 (see below) to yield 89 g (57%) of 4-cyanobenzylammonium methanesulphonate with a HPLC purity of 96.1 ae %.

EXAMPLE 4
Recrystallisation of Crude 4-Cyanobenzylammonium Methanesulphonate Crude 4-cyanobenzylammonium methanesulphonate crude (25.0 kg; 110 mol; purity 96.5 ae %; obtained as in Example 2) was dissolved in ethanol (86 L) at reflux. The solution was cooled slowly to approximately 20° C. The crystals which formed were centrifuged, washed with a small amount of ethanol (10 L) and dried to yield 20.4 kg (85%) of 4-cyanobenzylammonium methanesulphonate with a HPLC purity of >99.5 ae %.

EXAMPLE 5
Recrystallisation of Crude 4-Cyanobenzylammonium Methanesulphonate Crude 4-cyanobenzylammonium methanesulphonate (29.35 g; 129 mmol; obtained as in Example 1), which was found to contain small amounts of 1,4-di(ammoniummethyl)benzene bismethanesulphonate impurity, was dissolved in ethanol (150 mL) at reflux. The slurry was filtered at reflux temperature to remove the 1,4-di(ammoniummethyl)benzene bismethanesulphonate. The mother liquor was cooled slowly to approximately 20° C. The crystals which formed were filtered, washed with a small amount ethanol and dried to yield 26.1 g (89%) of 4-cyanobenzylammonium methanesulphonate with a purity of 96.0 ae %.

EXAMPLE 6
Recrystallisation of Crude 4-Cyanobenzylammonium Methanesulphonate Crude 4-cyanobenzylammonium methanesulphonate (5.0 g; 22 mmol), containing small amounts of 1,4-di(ammoniummethyl) benzene bismethanesulphonate impurity was dissolved in iso-propanol (225 mL) at reflux. The slurry was filtered at reflux temperature to remove the 1,4-di(ammoniummethyl)benzene bismethanesulphonate impurity, and the mother liquor was cooled slowly to approximately 20° C. The crystals which formed were filtered, washed with a small amount in iso-propanol and dried to yield 3.26 g (65%) of 4-cyanobenzylammonium methanesulphonate with a purity of 96.3 ae %.

Abbreviation:

ae %=area percent

What is claimed is:

1. A lower alkanesulphonate salt of a cyanobenzylamine.
2. A salt as claimed in claim 1 wherein the alkanesulphonate is a $C_{1-6}$ alkanesulphonate.
3. A salt as claimed in claim 2 wherein the alkanesulphonate is a $C_{1-3}$ alkanesulphonate.
4. A salt as claimed in claim 3, wherein the alkanesulphonate is ethanesulphonate or methanesulphonate.
5. A salt as claimed in claim 1, wherein the cyanobenzylamine is optionally substituted by one or more substituents selected from the group consisting of: halo, lower alkyl (which alkyl group is optionally substituted by one or more halo group), hydroxy, lower alkoxy, $—O(CH_2)_pC(O)N(R^a)(R^b)$ (in which p is 0, 1, 2, 3 or 4, and $R^a$ and $R^b$ independently represent H, lower alkyl or lower cycloalkyl), $N(R^c)R^d$ (in which $R^c$ and $R^d$ independently represent H, lower alkyl or $C(O)R^e$ (in which $R^e$ represents H and lower alkyl)), or $SR^f$ (in which $R^f$ represents H or lower alkyl).
6. A salt as claimed in claim 1, wherein the cyanobenzylamine is a 4-cyanobenzylamine.
7. A salt as claimed in claim 6, wherein the 4-cyanobenzylamine is unsubstituted 4-cyanobenzylamine.
8. A salt as claimed in claim 1, wherein the stoichiometric ratio of alkanesulphonate to cyanobenzylamine is between 1.0:0.9 and 1.0:1.1.
9. A salt as claimed in claim 8, wherein the stoichiometric ratio is between 1.0:0.95 and 1.0:1.05.
10. A process for the production of a salt according to claim 1 which comprises the selective crystallisation of a cyanobenzylamine with a lower alkanesulphonic acid.
11. A process as claimed in claim 10, wherein the solvent from which the salt is crystallised is a lower alkyl alcohol.
12. A process as claimed in claim 11, wherein the solvent is iso-propanol.
13. A process for the production of a salt according to claim 1, which comprises a selective hydrogenation of a dicyanobenzene in the presence of a $C_{3-5}$ alkyl alcohol, followed by a selective crystallization of a cyanobenzylamine with a lower alkanesulfonic acid.
14. A process as claimed in claim 13 which comprises, after the hydrogenation, and before the crystallisation, are carried out, the additional steps of (i) filtration of the reaction mixture, (ii) evaporation of a portion of the reaction solvent, and/or (iii) the preliminary addition of lower alkanesulphonic acid, followed by filtration or centrifugation.
15. A process as claimed in claim 13, wherein the alcohol is iso-propanol.

* * * * *